(12) United States Patent
Ikeda et al.

(10) Patent No.: US 6,520,908 B1
(45) Date of Patent: Feb. 18, 2003

(54) ELECTRONIC ENDOSCOPE

(75) Inventors: Yuichi Ikeda, Tama (JP); Hiroyuki Fukuda, Hino (JP)

(73) Assignee: Olympus Optical Co., Ltd. (JP)

( * ) Notice: Subject to any disclaimer, the term of this patent is extended or adjusted under 35 U.S.C. 154(b) by 130 days.

(21) Appl. No.: 09/671,560

(22) Filed: Sep. 27, 2000

(30) Foreign Application Priority Data

Sep. 30, 1999 (JP) .......................................... 11-280432

(51) Int. Cl.$^7$ ................................................. A61B 1/00
(52) U.S. Cl. ......................... 600/132; 600/110; 600/158
(58) Field of Search ................................. 600/132, 110, 600/158, 159, 131; 385/118

(56) References Cited

U.S. PATENT DOCUMENTS

| 4,765,312 A | * | 8/1988 | Sasa et al. ..................... 128/4 |
| 5,458,132 A | * | 10/1995 | Yabe et al. ................... 600/121 |
| 5,702,349 A | | 12/1997 | Morizumi .................... 600/131 |
| 5,876,326 A | * | 3/1999 | Takamura et al. ........... 600/110 |
| 5,993,381 A | * | 11/1999 | Ito ............................... 600/131 |

* cited by examiner

*Primary Examiner*—Denise L. Esquivel
*Assistant Examiner*—Marc Norman
(74) *Attorney, Agent, or Firm*—Ostrolenk, Faber, Gerb & Soffen, LLP

(57) ABSTRACT

An electronic endoscope in accordance with the present invention consists broadly of an operation unit, an elongated insertion unit, and a universal cord. The operation unit has a treatment appliance insertion port and various operation switches and fills the role of a hand-held unit. The insertion unit extends from the lower end of the operation unit in a direction substantially corresponding to the longitudinal direction of the operation unit. The universal cord extends in a direction crossing the longitudinal direction of the operation unit at an acute angle, and accommodates at least a signal cable extending from the top of the operation unit.

46 Claims, 9 Drawing Sheets

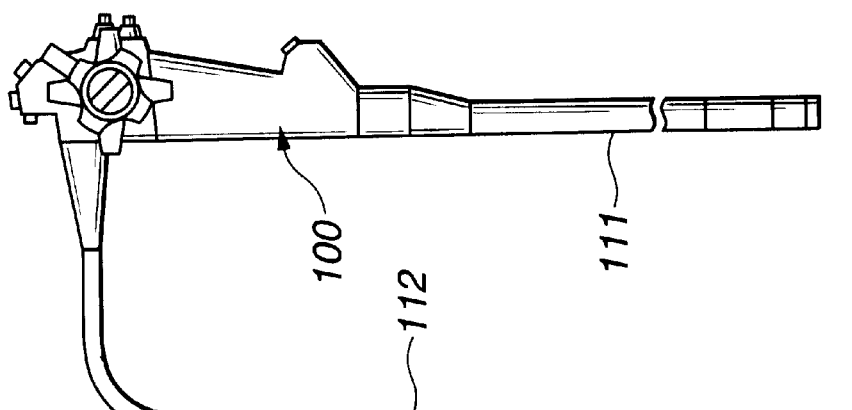
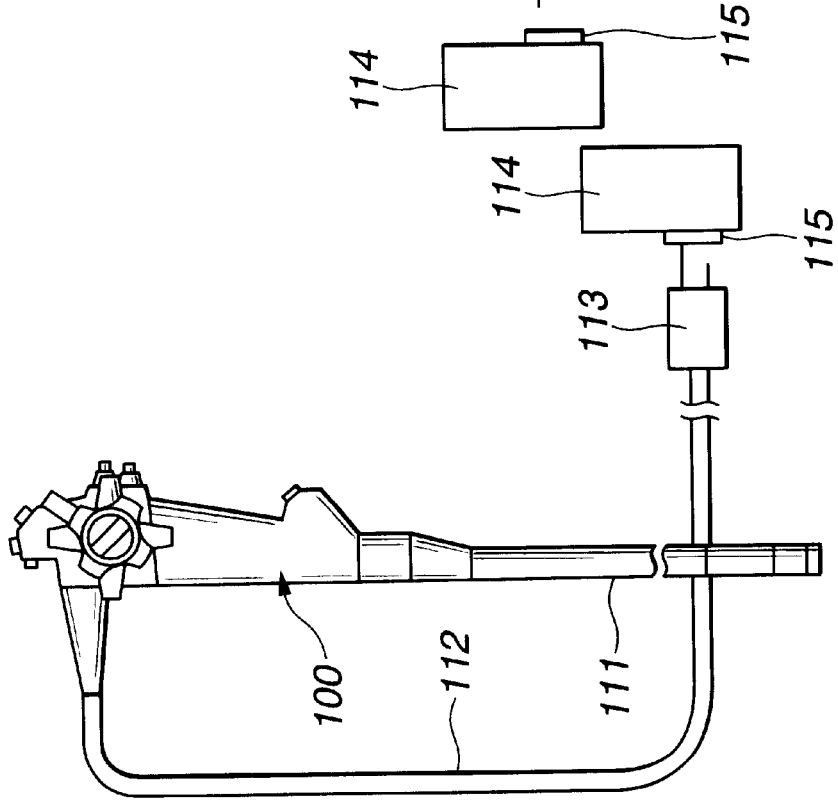

ELECTRONIC ENDOSCOPE

This application claims benefit of Japanese Application No. Hei 11-280432 filed in Japan on Sep. 30, 1999, the contents of which are incorporated by reference.

BACKGROUND OF THE INVENTION

1. Field of the Invention

The present invention relates to an electronic endoscope having a treatment appliance insertion port and various operation switches formed in and on an operation unit thereof, and having a universal cord extended from the operation unit.

2. Description of the Related Art

In recent years, endoscopes having an elongated insertion unit inserted into a body cavity and having, if necessary, a treatment appliance passed through a treatment appliance channel so as to enable various kinds of examinations and treatments have widely been adopted. The endoscopes include an electronic endoscope having a solidstate imaging device such as a charge-coupled device (CCD) incorporated as an imaging means therein. The electronic endoscope converts an optical image of an object converged on the CCD into an electric signal and the electric signal into an image signal, displays an image of the object on the screen of a monitor, and thus enables observation of a lesion or the like.

A type of electronic endoscope has a soft insertion unit that includes a bending portion formed by concatenating a plurality of bending pieces. The bending portion can be angled vertically and laterally. The insertion unit can therefore be inserted into a tortuous body cavity through the oral cavity or anus. Angling the bending portion is controlled using an angling knob that is one of operation switches formed on an operation unit communicating with the proximal end of the insertion unit and filling the role of a hand-held unit.

Moreover, a universal cord accommodating a signal cable extended from the CCD or operation switch and a light guide fiber bundle is extended from a flank of the operation unit. A connector is attached to one end of the universal cord. Consequently, the universal cord is coupled to a camera control unit (hereinafter a CCU) that is an external apparatus through the connector so that the universal cord can be uncoupled freely.

The CCU has a light source and a signal processor, which are not shown, incorporated therein. The light source supplies illumination light to the electronic endoscope. The signal processor processes an electric signal photoelectrically converted from an optical image of an object by the solid-state imaging device incorporated in the distal part of the insertion unit. When the universal cord is coupled to the CCU through the connector, it becomes possible to transfer the electric signal or supply illumination light.

As shown in FIG. 1, an operation unit 100 of a conventional electronic endoscope consists of a hand-held portion 101 and an operator portion 102 located proximally to the hand-held portion 101 (upside in the drawing). The operator portion 102 has a suction button 103, an aeration/perfusion button 104, and other pushbutton switches included in operation switches, and angling knobs 105 and 106 that are also referred to as operation switches and used to angle the bending portion, which is not shown, of an insertion unit 111. Control switches 107, 108, 109, and 110 that are also referred to as operation switches are formed near the end of the hand-held portion 101 and used to control display of an endoscopic image on a display device that is not shown.

The operation unit 100 is designed to be preferably held with the left hand. A user holds the middle portion, which is not shown, of the insertion unit 111 with his/her right hand. The user introduces the distal part of the insertion unit 111 to a region to be observed in a body cavity while handling the angling knobs 105 and 106 with the fingers of his/her left hand. Otherwise, a user holds the insertion unit 111 with his/her right hand, and handles the suction button 103, aeration/perfusion button 104, and various control switches 107, 108, 109, and 110 with his/her left hand.

A user can handle the operation switches with the fingers of his/her left hand without parting his/her right hand from the insertion unit 111. The user can efficiently introduce the insertion unit 111 to a region to be observed. Moreover, since it is unnecessary to handle the various operation switches on the operator portion 102 with the wet right hand, the insertion unit 111 remains sanitary.

However, as shown in FIG. 1, a universal cord 112 having high springiness extends in a direction substantially orthogonal to the longitudinal direction of the operation unit 100. When the insertion unit 111 is introduced into a body cavity, if the insertion unit 111 is, as shown in FIG. 2, twisted in a direction of arrow A, the universal cord 112 is bent to wind about the operation unit 100. Since the universal cord 112 has springiness, the universal cord 112 bent to wind about the operation unit imposes a load, which constrains the operation unit 100 to return to its original position, on the operation unit 100. At this time, an operator must handle the operation unit 100 against the load. An unnecessarily large magnitude of force is therefore needed to manipulate the endoscope.

A discussion will be made of a case where a connector 113 attached to the proximal end of the universal cord 111 as shown in FIG. 3A and FIG. 3B is mated with a light source connector 115 formed on a CCU 114.

For example, assume that the CCU 114 is, as shown in FIG. 3A, installed to the left side of the electronic endoscope. For matching the upper and lower sides of the connector 113 attached to the universal cord 112 with those of the light source connector 115 formed on the CCU 114, the universal cord 112 must be turned 180° to form a twist 116. The formation of the twist 116 brings about a fear that an unnecessarily large magnitude of force may be required to introduce the endoscope into a body cavity, thus invariably increasing the burden on the operator. For overcoming this drawback, the CCU 114 must be installed to have the positional relationship relative to the electronic endoscope shown in FIG. 3B.

Furthermore, when an attempt is made to handle any of the various control switches 107, 108, 109, and 110, aeration/perfusion button 104, suction button 103, and angling knobs 105 and 106 formed on the operation unit 100, a force with which the hand-held portion 101 is held may be gone. This poses a problem in that the held state of the operation unit 100 can become unstable.

A treatment appliance insertion port 117 (see FIG. 1) formed in the operation unit 100 and used to introduce a treatment appliance into a body cavity is located distally to the various control switches 107, 108, 109, and 110, suction button 103, and aeration/perfusion button 104 with the hand-held portion 101 between them. Therefore, when the insertion unit 111 is held with the right hand and the operation unit 100 is held with the left hand, it is hard to manipulate a treatment appliance such as forceps introduced into a body cavity through the treatment appliance insertion port 117. For manipulating the treatment appliance, a nurse or the like is usually asked to hold the insertion unit 111. However, when a nurse holds the insertion unit 111, an endoscopic image of an operator-intended region to be observed is hard to produce.

In efforts to improve maneuverability of an endoscope, various proposals have been disclosed in, for example, Japanese Unexamined Patent Application Publication Nos. 8-19507 and 7-100105, Japanese Unexamined Utility Model Publication No. 60-171403, and Japanese Examined Utility Model Publication No. 63-23042.

SUMMARY OF THE INVENTION

Accordingly, an object of the present invention is to provide an electronic endoscope having the characteristics of a stable hold, excellent user-friendliness, and superb maneuverability.

Briefly, an electronic endoscope in accordance with the present invention consists broadly of an operation unit, an elongated insertion unit, and a universal cord. The operation unit has a treatment appliance insertion port and various operation switches and fills the role of a hand-held unit. The insertion unit extends from the lower end of the operation unit in a direction substantially corresponding to the longitudinal direction of the operation unit. The universal cord extends from an upper part of the operation unit in a direction crossing the longitudinal direction of the operation unit at an acute angle, and accommodates at least a signal cable.

BRIEF DESCRIPTION OF THE DRAWINGS

FIG. 1 to FIG. 3 are explanatory diagrams concerning a conventional electronic endoscope;

FIG. 1 is an explanatory diagram concerning the components of an operation unit of the electronic endoscope;

FIG. 2 is an explanatory diagram concerning the relationship between the operation unit and a universal cord established when an insertion unit is twisted;

FIG. 3A and FIG. 3B are explanatory diagrams concerning the state of the universal cord that varies depending on the positional relationship between the electronic endoscope and a CCU;

FIG. 3A shows a positional relationship causing the universal cord to form a twist;

FIG. 3B shows a positional relationship causing the universal cord to form no twist;

FIG. 4 to FIG. 8 are concerned with the first embodiment of the present invention;

FIG. 4A is an oblique view for explaining the components of the electronic endoscope;

FIG. 4B is an explanatory diagram concerning the appearance of an operation unit of the electronic endoscope and its surroundings with the endoscope viewed from its frontal direction;

FIG. 4C is an explanatory diagram concerning the appearance of the operation unit of the electronic endoscope and its surroundings with the endoscope viewed from its lateral direction;

FIG. 5A is a sectional view for explaining the structure of the joint between the universal cord and operation unit;

FIG. 5B is a cross-sectional view showing a plane A—A shown in FIG. 5A;

FIG. 6A is an explanatory diagram concerning the twisted state of the universal cord;

FIG. 6B is an explanatory diagram concerning the universal cord whose twisted state has been corrected;

FIG. 7 is an explanatory diagram concerning an operation to be exerted by the electronic endoscope when the insertion unit is twisted;

FIG. 8 is an explanatory diagram concerning an operation to be exerted by the electronic endoscope having a treatment appliance insertion port formed between an aeration/perfusion button and a suction button;

FIG. 9A is an oblique view for explaining the components of the electronic endoscope;

FIG. 9B is an explanatory diagram concerning the appearance of an operation unit of the electronic endoscope and its surroundings with the endoscope viewed from its frontal direction;

FIG. 9C is an explanatory diagram concerning the appearance of. the operation unit of the electronic endoscope and its surroundings with the endoscope viewed from its lateral direction;

FIG. 10A shows a case where the operation unit and universal cord share the same plane;

FIG. 10B shows another case where the operation unit and universal cord share the same plane;

FIG. 11A is an oblique view showing the operation unit and its surroundings; and FIG. 11B is a diagram for practically explaining an operation to be exerted by the universal cord.

DESCRIPTION OF THE PREFERRED EMBODIMENTS

Figure 1:
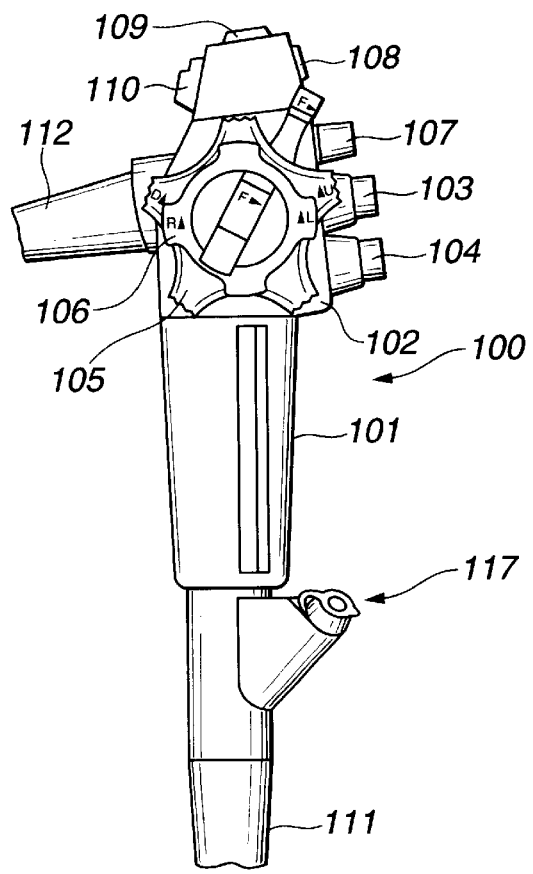
Figure 2:
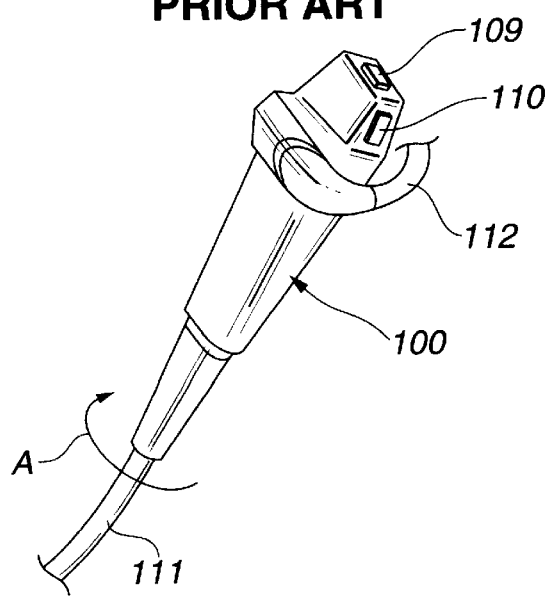

Referring to the drawings, embodiments of the present invention will be described below.

The first embodiment of the present invention will be described with reference to FIG. 4A to FIG. 8.

Figure 4A:
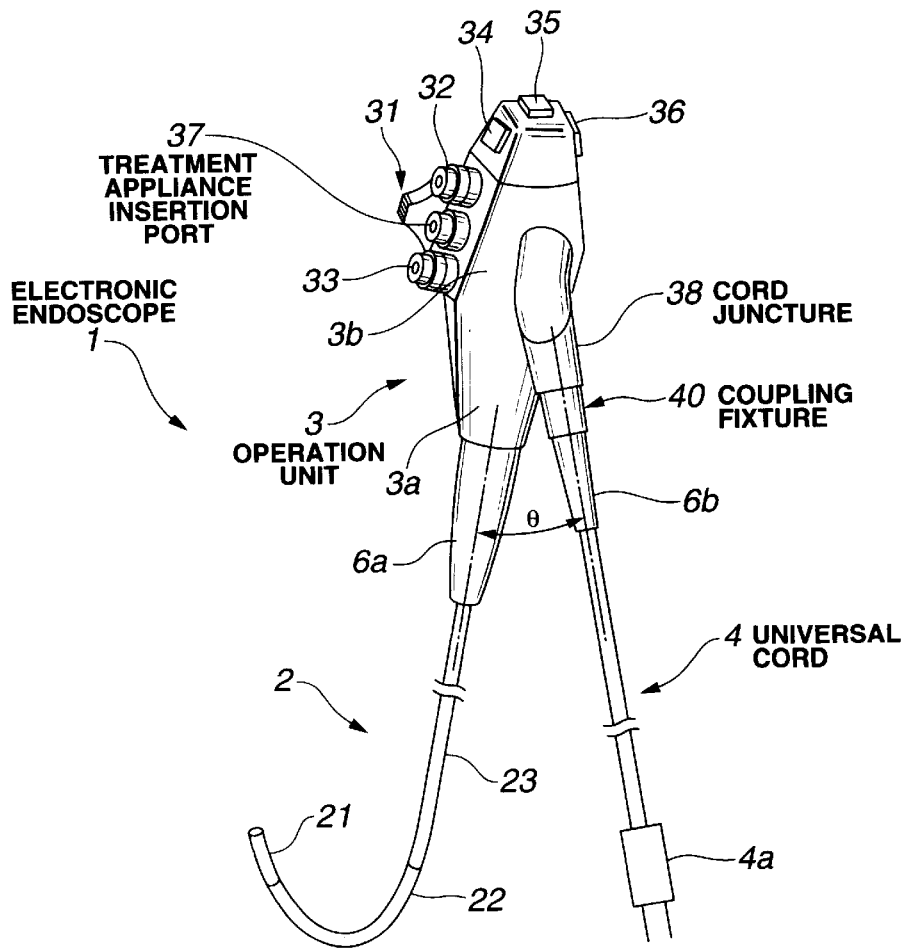
FIG. 4A to FIG. 4C are explanatory diagrams concerning the components of an electronic endoscope.

An electronic endoscope (hereinafter simply an endoscope) 1 in accordance with the present embodiment shown in FIG. 4A is designed for, for example, medical use. The endoscope 1 consists mainly of an elongated insertion unit 2 to be inserted into a body cavity, an elongated operation unit 3 formed proximally to the insertion unit 2 and filling the role of a hand-held unit, and a universal cord 4 extending from the operation unit 3.

The insertion unit 2 is extended from the distal end of the operation unit 3 in a direction substantially corresponding to the longitudinal direction of the operation unit 3. The insertion unit 2 has a rigid distal part 21, a bending portion 22, and a flexible tube 23 arranged in that order from the distal end thereof. The distal part 21 has a built-in imaging device that is not shown. The bending portion 22 has a plurality of bending pieces concatenated and can be angled vertically and laterally. The flexible tube 23 has flexibility.

The operation unit 3 consists of a hand-held portion 3a to be held by an operator and an operator portion 3b located proximally to the hand-held portion 3a (upside in the drawing). The operator portion 3b has operation switches formed thereon in a watertight fashion. The operation switches include an angling knob 31 used to angle the bending portion 22, pushbutton switches such as a suction button 32 and an aeration/perfusion button 33, and control switches 34, 35, and 36 used to control display of an endoscopic image on a display device that is not shown.

A treatment appliance insertion port 37 through which a treatment appliance such as forceps is introduced into a body cavity over a suction channel is formed between the aeration/perfusion button 33 and suction button 32.

Moreover, a cord juncture 38 at which the universal cord 4 is coupled and fixed to the operation unit 3 is projected from one flank of the operation unit 3. The cord juncture 38 meets the operation unit 3 at an acute angle (θ) with respect to the longitudinal direction of the operation unit 3.

Figure 4B:
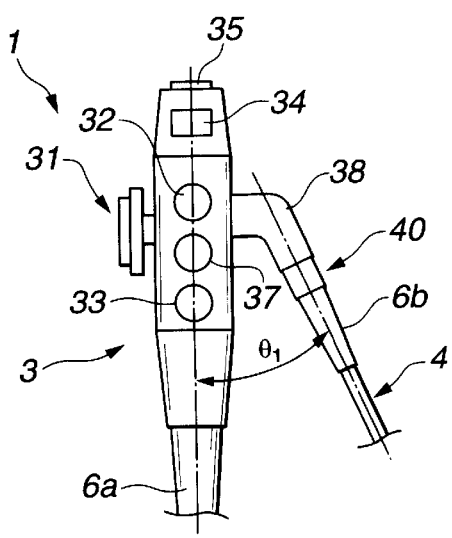
Figure 4C:
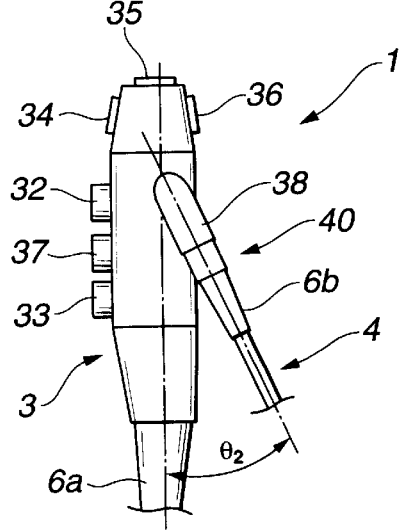

A crossed-axes angle θ1 shall be, as shown in FIG. 4B, an angle formed on a plane containing the face of the endoscope between the longitudinal axis of the operation unit and the longitudinal axis of the universal cord on the assumption that the universal cord 4 is extended straight. A crossed-axes angle θ2 shall be, as shown in FIG. 4C, an angle formed,on a plane containing one flank of the endoscope between the longitudinal axis of the operation unit and the longitudinal axis of the universal cord. The crossed-axes angles θ1 and θ2 are acute angles.

Consequently, the insertion unit 2 and universal cord 4 are extended downwards in FIG. 4A, FIG. 4B, and FIG. 4C.

An operator's left hand with which the operation unit 3 is held is rested on part of one flank of the operation unit 3 between the operation unit 3 and the cord juncture 38 and a coupling fixture 40 attached to an end of the universal cord 4. The cord juncture 38 and coupling fixture 40 therefore traverses the back of the operator's left hand. According to the present embodiment, the cord juncture 38 and coupling fixture 40 constitute a hold assistant against which the operator's left hand is rested.

The coupling fixture 40 attached to one end of the universal cord 4 serves as an integral part of not only the hold assistant but also a cord twist correcting means. The coupling fixture 40 is joined to the cord juncture 38 formed on the operation unit 3, whereby the universal cord 4 can be rotated 180° or more as mentioned later. Moreover, a connector 4a is attached to the other end of the universal cord 4. The connector 4a is coupled to a camera control unit 5 (see FIG. 6) (hereinafter a CCU) that is an external apparatus so that it can be uncoupled freely.

A signal line and a light guide fiber bundle or the like are passed through the universal cord 4, operation unit 3, and insertion unit 2. The signal line links an imaging device that is not shown and the CCU 5. Illumination light emanating from a light source, which is not shown, incorporated in the CCU 5 is propagated to the distal part 21 of the insertion unit 2 over the light guide fiber bundle. Moreover, anti-break members 6a and 6b are used to protect the insertion unit 2 and universal cord 4 respectively from buckling.

Figure 5A:
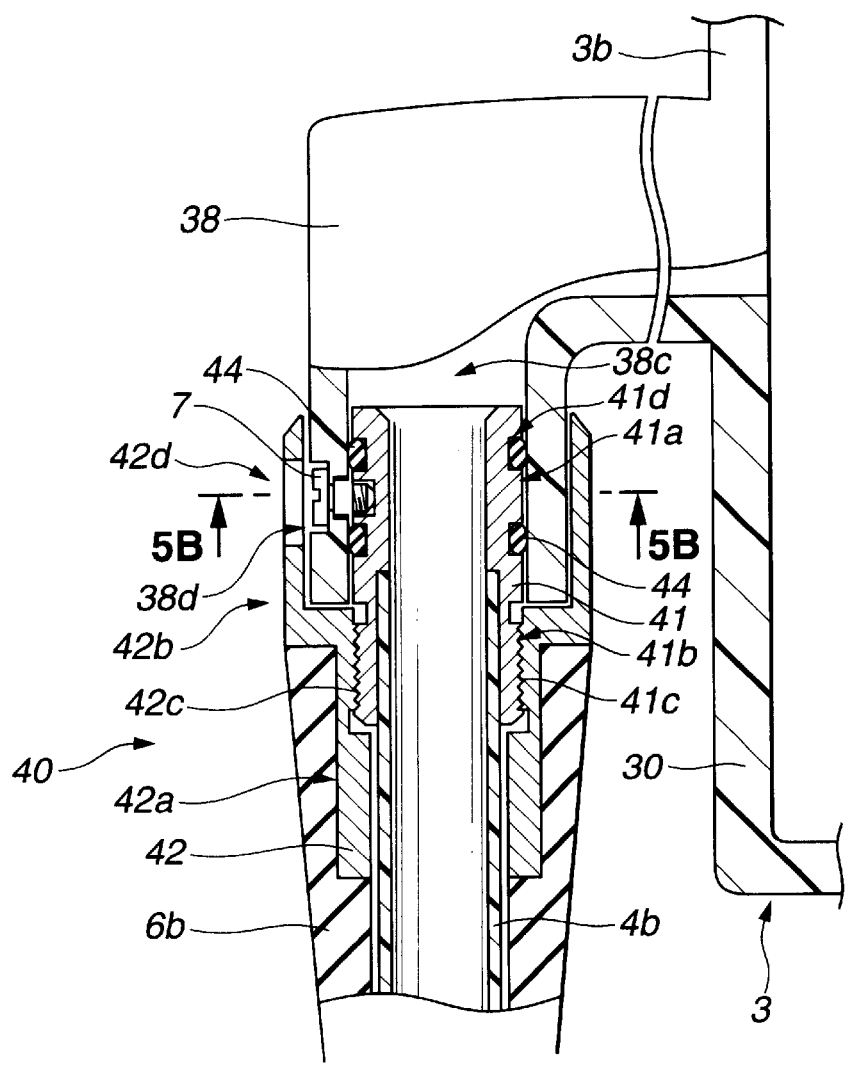
FIG. 5A and FIG. 5B are explanatory diagrams concerning the structure of a joint between a universal cord and the operation unit.
Figure 5B:
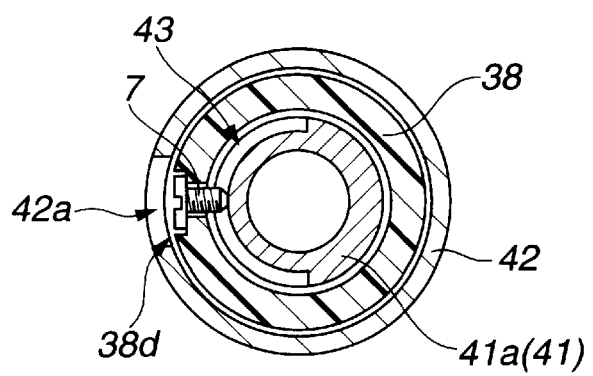

Referring to FIG. 5A and FIG. 5B, a description will be made of the structure of the cord twist correcting means composed of the cord juncture 38 and coupling fixture 40, and an operation to be exerted by the cord twist correcting means.

As shown in FIG. 5A, the cord juncture 38 projects from an operation unit body 30 of the operation unit 3. The light guide fiber bundle and signal line are passed through a hollow 38c of the cord juncture 38. A screw hole 38d having a female screw threaded on the inner wall thereof is bored at the end of the cord juncture 38. The female screw is mashed with a lock screw 7.

As shown in FIG. 5A and FIG. 5B, the coupling fixture 40 consists of a first coupling member 41 and a second coupling member 42. The first coupling member 41 is shaped like a pipe and composed of a rotator portion 41a and a joint portion 41b. The second coupling member 42 is a pile member having a small-diameter portion 42a, which is joined to the joint portion 41b of the first coupling member 41 and has a small diameter, and a large-diameter portion having a large diameter.

The rotator portion 41a of the first coupling member 41 is engaged with the hollow 38c of the cord juncture 38. The joint portion 41b is formed to project from the hollow 38c, and has, for example, a male screw 41c, which serves as a joint, threaded on the periphery thereof. The small-diameter portion 42a of the second coupling member 42 has a female screw 42c, which is meshed with the male screw 41c threaded on the joint portion 41b, threaded thereon. The large-diameter portion is a juncture shield 42b engaged with the periphery of the cord juncture 38. The large-diameter portion has a through hole 42d, through which the lock screw 7 is fitted into the screw hole 38d, formed at a predetermined position thereon.

A rotation groove 43 extending circumferentially is bored in the periphery of the rotator portion 41a of the first coupling member 41. The rotation groove 43 enables the universal, cord 4 to rotate substantially 180° or more relative to the operation unit.

A circumferential groove 41d in which an O ring 44 is fitted in order to maintain watertightness between the hollow of the cord juncture 38 and the periphery of the rotator portion 41a and induce a predetermined magnitude of resistance to a turn is formed on both sides of the rotation groove 43.

A cord member 4b that is an integral part of the universal cord 4 is locked in the hollow of the first coupling member 41, and the anti-break member 6b is mounted on the small-diameter portion 42a of the second coupling member 42 as an integral part thereof.

The male screw 41c threaded on the first coupling member 41 having the cord member 4b locked therein as an integral part thereof and having the O rings 44 fitted in the circumferential grooves 41d is meshed with the female screw 42c threaded on the second coupling member 42 having the anti-break member 6b mounted thereon as an integral part thereof. The coupling fixture 40 attached to one end of the universal cord 4 is thus realized.

Now, how to join the coupling fixture 40 and cord juncture 38 will be described below.

For joining the coupling fixture 40 to the cord juncture 38, first, the rotator portion 41a of the first coupling member 41 is thrust into the hollow 38c of the cord juncture 38 against constraining force exerted by the O rings 44.

Thereafter, the rotation groove 43 bored in the first coupling member 41 is substantially aligned with the screw hole 38d bored in the cord juncture 38 through the through hole 42d bored in the second coupling member 42.

The lock screw 7 is then fitted into the screw hole 38d through the through hole 42d, meshed with the female screw threaded on the wall of the screw hole 38d, and then tightened. The tip of the lock screw 7 is thus put in the rotation groove 43. Consequently, the rotator portion 41a is located at a predetermined position so that it can rotate freely.

Consequently, the second coupling member 42 having the anti-break member 6b mounted thereon as an integral part thereof is rotated. The first coupling member 41 joined to the second coupling member 42 is therefore guided to rotate by an angle determined with the length of the rotation groove 43 owing to the lock screw 7. Thus, the coupling fixture 40 rotates 180° or more.

Operations to be executed by the endoscope 1 having the foregoing structure will be described below.

Figure 6A:
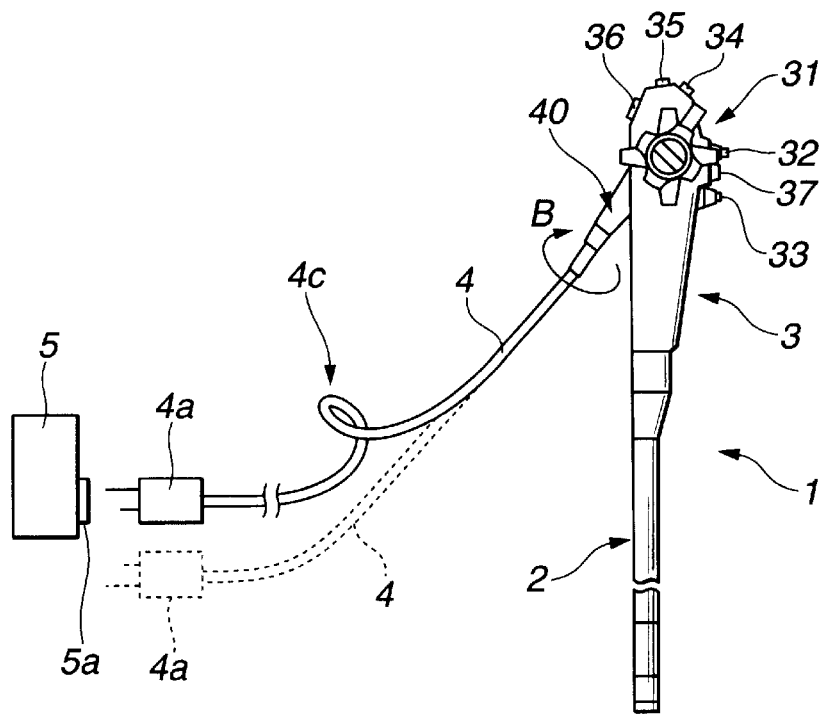
FIG. 6A and FIG. 6B are explanatory diagrams concerning an operation to be exerted by the electronic endoscope having a cord twist correcting means.
Figure 6B:
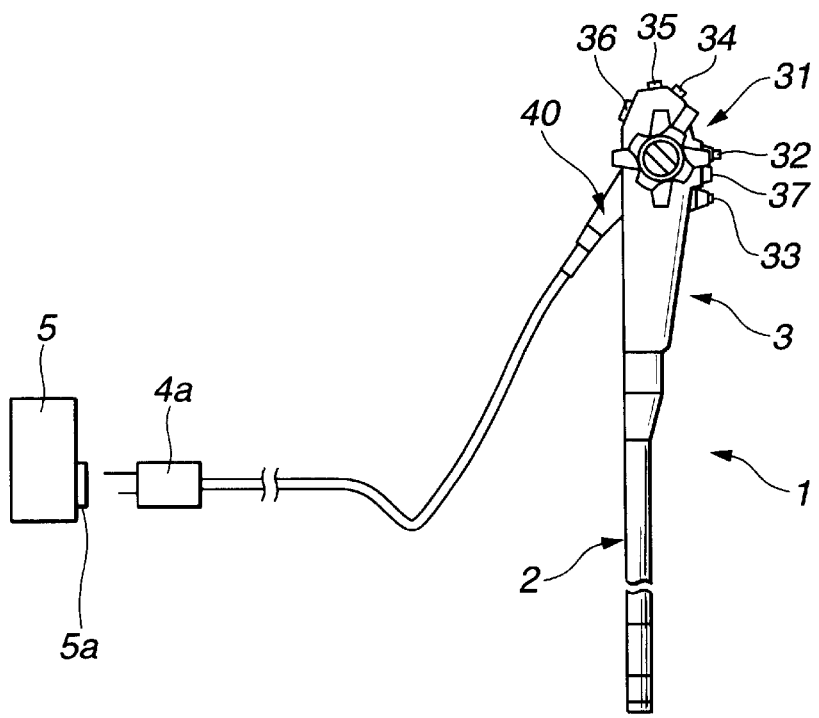

To begin with, an operation to be performed when the connector 4a attached to the end of the universal cord 4 extending from the operation unit 3 of the endoscope 1 is mated with a light source connector 5a of the CCU 5 will be described with reference to FIG. 6A and FIG. 6B.

When an attempt is made to connect the endoscope 1 to the CCU 5, the orientation of the connector 4a attached to the universal cord 4 may be reversed as indicated with dashed lines in FIG. 3A depending on the positional relationship between the endoscope 1 and CCU 5. When an attempt is made to adjust the orientation of the connector 4a as indicated with solid lines, the universal cord 4 may be twisted to form a twist 4c. This may hinder manipulation of the endoscope.

In the endoscope 1 of the present embodiment, the second coupling member 42 included in the coupling fixture 40 attached to one end of the universal cord 4 and having the anti-break member 6b mounted thereon as an integral part thereof is rotated 180° in a direction of arrow B. Consequently, the twist 4c of the universal cord 4 is unraveled as shown in FIG. 6B. The connector 4a can be smoothly mated with the light source connector 5a of the CCU 5.

As mentioned above, the coupling fixture 40 attached to the universal cord is joined to the cord juncture 38 formed on the operation unit so that the coupling fixture can rotate at least 180°. It will therefore not happen when the connector of the electronic endoscope is mated with the light source connector of the CCU, that the universal cord is twisted to form a twist. This contributes to improvement in the maneuverability of the electronic endoscope.

Figure 7:
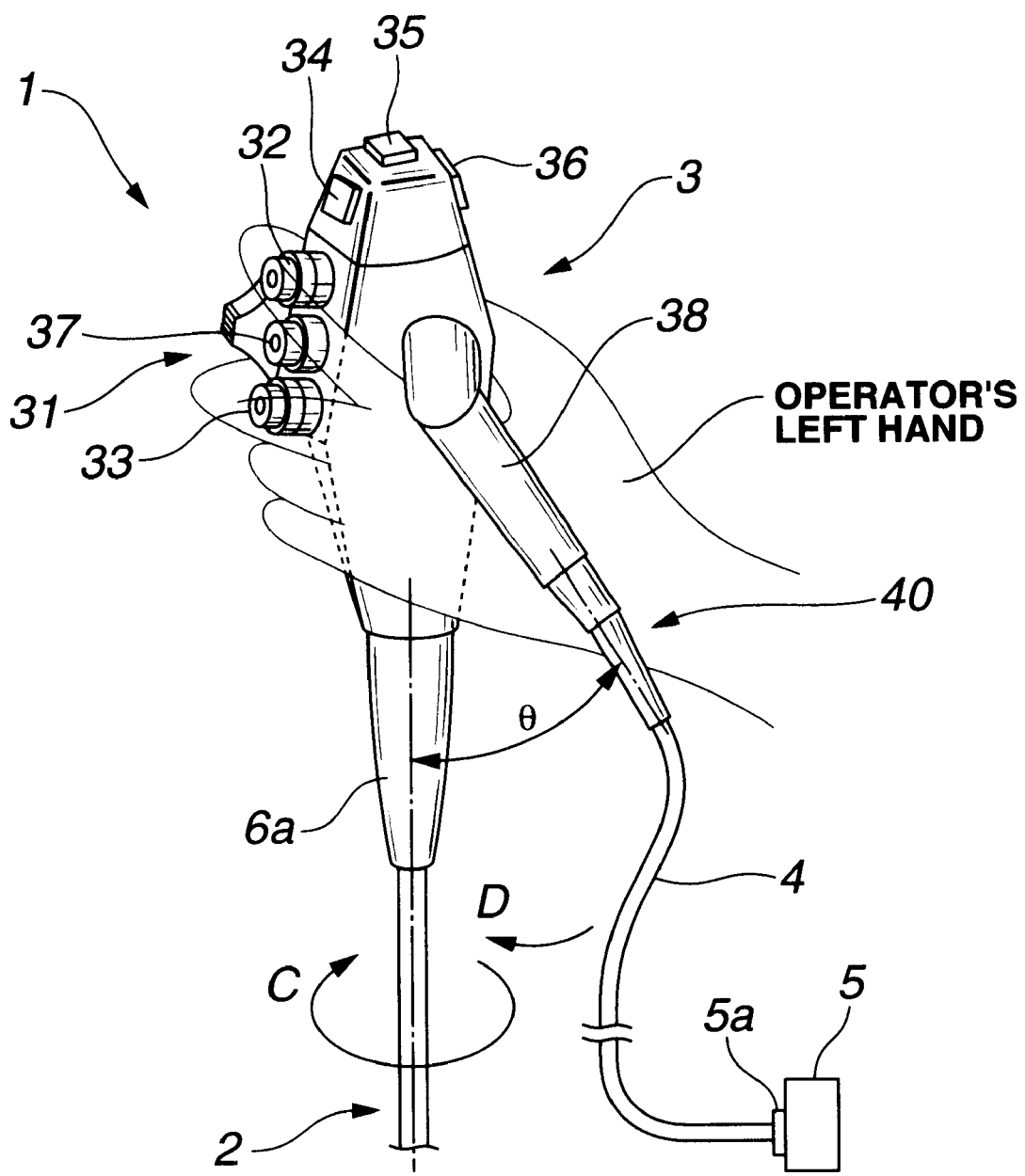

Next, an operation to be performed when an operator holds the endoscope 1 and inserts the insertion unit 2 into a body cavity will be described with reference to FIG. 7.

When an operator holds the endoscope, the operator's left hand is rested on the part of one flank of the operation unit 3 between the flank and the combination of the cord juncture 38 and coupling fixture 40 attached to one end of the universal cord 4. At this time, when the state of the left hand with which the operation unit is held is changed, the back of the operator's left hand rests against a rigid support structure defined by the combination of the cord juncture 38 and coupling fixture 40. The endoscope 1 is therefore held on a stable basis while being supported at two points, that is, with the palm of the left hand with which the operation unit 3 is held and the back of the left hand resting against the end of the universal cord 4.

With the operation unit held in this say, the distal part 21 of the insertion unit 2 is inserted into a region to be observed at the sight of an endoscopic image displayed on the screen of a monitor that is not shown. At this time, if necessary, an operator twists the insertion unit 2 in a direction of arrow C as shown in FIG. 7.

The cord juncture 38 formed on the operation unit 3 is extended at an acute angle θ with respect to the longitudinal axis of the operation unit 3. The universal cord 4 coupled to the cord juncture 38 with the coupling fixture 40 between them so that the universal cord 4 can rotate freely is extended with the acute angle θ retained with respect to the longitudinal axis of the operation unit 3. Therefore, even when the insertion unit 2 is twisted, the universal cord 4 will not be bent to impose a load on the operation. unit 3 but will move towards the insertion unit 2 as indicated with an arrow D.

In other words, when the insertion unit 2 is twisted, the universal cord 4 merely moves around the insertion unit 2. The endoscope can therefore be manipulated with the operation unit 3 free from any load stemming from the springiness of the universal cord 4.

As mentioned above, the cord juncture to which the coupling fixture attached to one end of the universal cord is joined is formed at the acute angle θ with respect to the longitudinal axis of the operation unit so that the universal cord will extend in a direction substantially corresponding to the direction of extension of the insertion unit (downside in the drawing). A drawback attributable to the fact that when the insertion unit is twisted, a load is imposed on the operation unit because of the springiness of the universal cord can be overcome.

Moreover, the cord juncture is formed at the acute angle θ with respect to the longitudinal axis of the operation unit, and the coupling fixture attached to one end of the universal cord is joined to the cord juncture. When an operator holds the operation unit, the cord juncture and coupling fixture are located near the back of the operator's left hand and serve as a hold assistant. The electronic endoscope can therefore be supported at two points, that is, with the back and palm of the left hand. This contributes to great improvement in the stability of a hold on the electronic endoscope.

Next, an operation to be executed when a treatment appliance is passed through the treatment appliance insertion port 37 interposed between the suction button 32 and aeration/perfusion button 33 will be described with reference to FIG. 8.

When the distal part 21 of the insertion unit 2 of the endoscope 1 is opposed to a region to be observed, an endoscopic image of the region to be observed displayed on the screen of a monitor that is not shown is viewed. A treatment is then performed if necessary. At this time, an operator parts his/her right hand from the insertion unit 2 and passes a treatment appliance 8 through the treatment appliance insertion port 37.

When the treatment appliance has reached a predetermined position, the operator holds the insertion unit 2 with his/her right hand and visualizes the region to be observed on the screen of the monitor.

Figure 8:
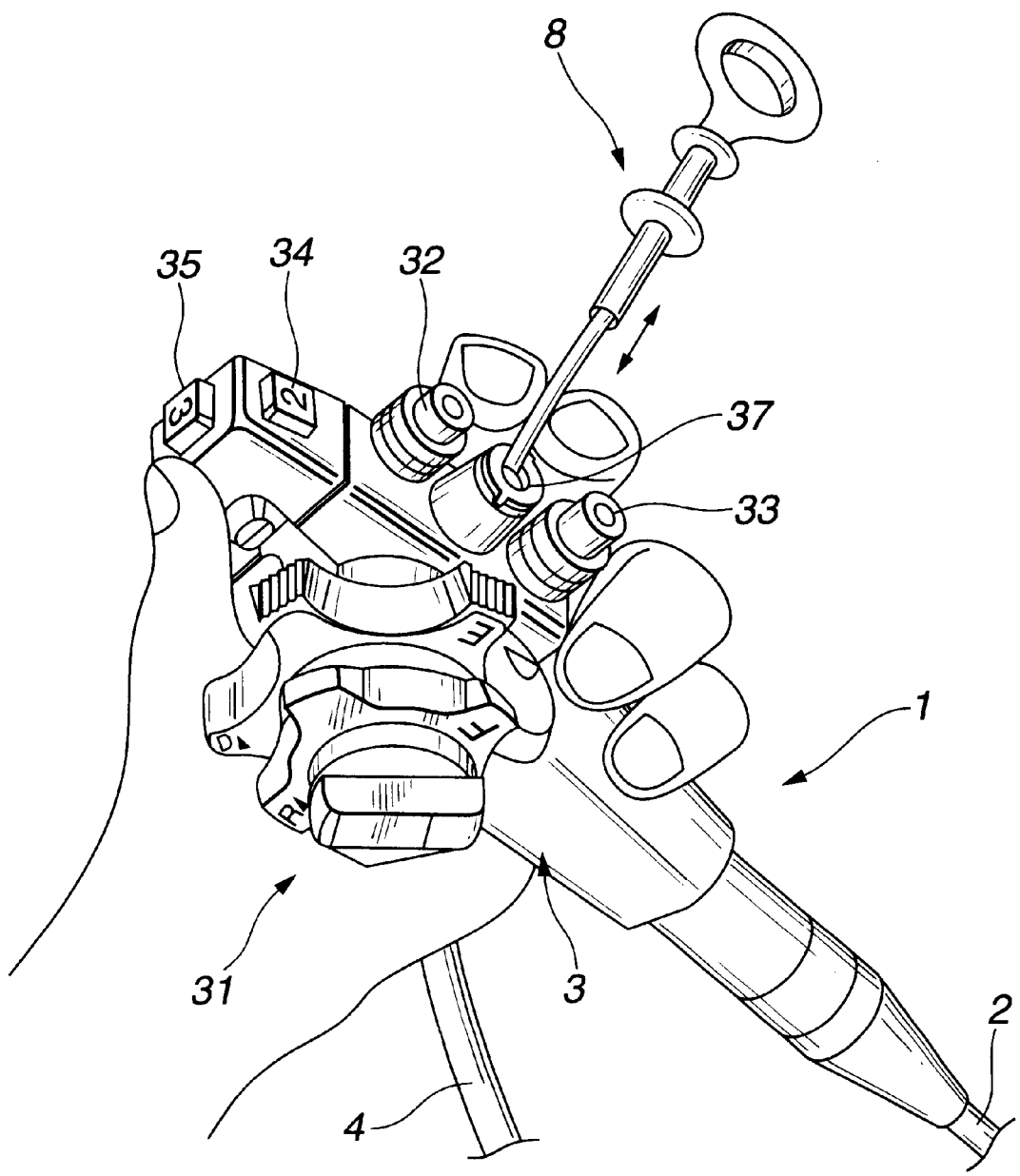

With the treatment appliance 8 borne with the index and middle fingers of the left hand, the treatment appliance 8 is advanced or withdrawn as indicated with the double-sided arrow in FIG. 8 so that it will be visualized on the screen of the monitor. When the treatment appliance 8 is opposed to an intended region, the treatment appliance 8 is manipulated with the index and middle fingers of the left hand in order to perform a predetermined treatment.

In other words, an operator can swiftly introduce the treatment appliance 8 to a predetermined position so as to perform a treatment while holding the insertion unit 2 with his/her right hand without the necessity of parting his/her left hand from the operation unit 3. Namely, the operator can swiftly introduce the treatment appliance 8 without disturbing an endoscopic image displayed on the screen of the monitor.

The treatment appliance insertion port through which a treatment appliance is introduced into a body cavity is interposed between the suction button and aeration/perfusion button to be handled with the index and middle fingers respectively. A treatment appliance put into the treatment appliance insertion port can be manipulated with the index and middle fingers without the necessity of changing the positions of the operator's right and left hands. This contributes greatly to improvement in the maneuverability of the endoscope.

Referring to the drawing concerning the present embodiment, the suction button 32, aeration/perfusion button 33, and treatment appliance insertion port 37 are juxtaposed straight on the surface of the operation unit illustrated upside in the drawing. The positional relationship among the suction button 32, aeration/perfusion button 33, and treatment appliance insertion port 37 is determined in consideration of maneuverability. Their location is not limited to the surface of the operation unit illustrated in the drawing, and their layout is not limited to the straight juxtaposition.

Moreover, when it is intended to manipulate the treatment appliance 8, if the endoscope 1 is held with the back of the left hand rested against the hold assistant, the treatment appliance 8 can be manipulated more smoothly.

The first embodiment has been described on the assumption that the endoscope is an electronic endoscope for medical use. The endoscope is not limited to the one for medical use but may be the one for industrial use.

Figure 9A:
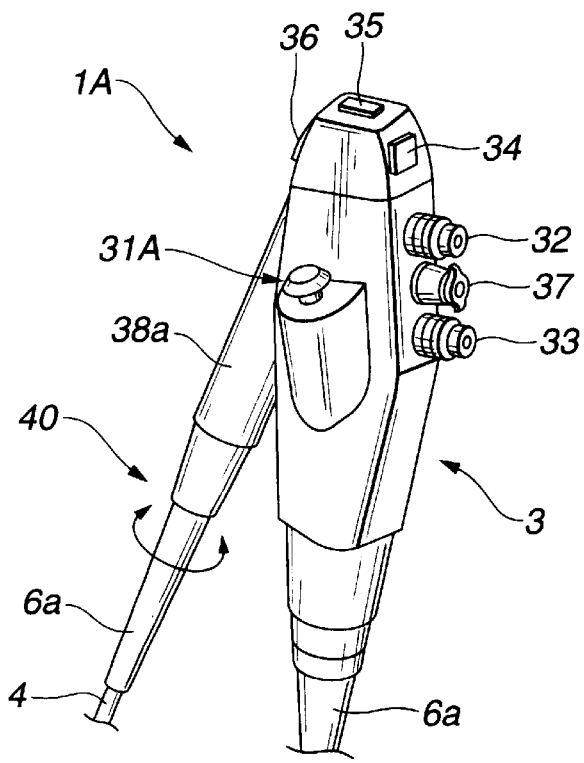
FIG. 9A to FIG. 9C are explanatory diagrams concerning the structure of a joint between an operation unit and a universal cord included in an electronic endoscope in accordance with the second embodiment of the present invention.
Figure 9B:
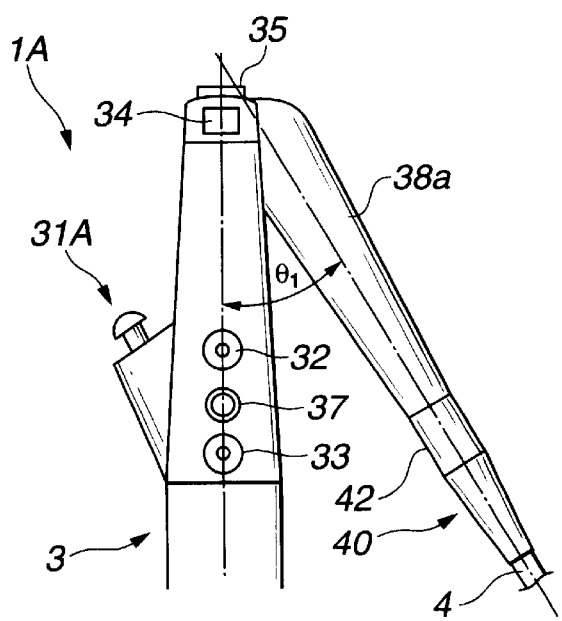
Figure 9C:
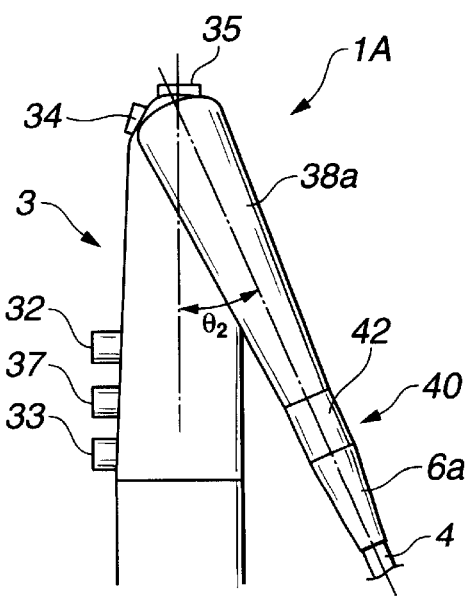

The second embodiment of the present invention will be described with reference to FIG. 9A to FIG. 9C.

In the endoscope 1 of the first embodiment, the cord juncture 38 is projected from the middle point of the operation unit 3. In contrast, in an endoscope 1A of the present embodiment, a cord juncture 38a is projected from the proximal end of the operation unit 3 as shown in FIG. 9A, FIG. 9B, and FIG. 9C. At this time, the longitudinal axes of the cord juncture and operation unit form an acute angle θ1 on a plane containing the face of the endoscope. Moreover, the longitudinal axes of the cord juncture and operation unit form an acute angle θ2 on a plane containing one flank of the endoscope. The coupling fixture 40 attached to one end of the universal cord 4 is joined to the cord juncture 38a.

A joystick 31A used to angle the bending portion 22 is formed instead of the angling knob 31, which is one of the operation switches, on one flank of the operation unit 3. The other components are identical to those of the first embodiments. The same reference numerals are assigned to the identical components, and the description of the components is omitted.

As mentioned above, the cord juncture to which the coupling fixture attached to one end of the universal cord is joined is projected from the proximal end of the operation unit at an acute angle. Consequently, the insertion unit extending from the operation unit and the universal cord can be balanced easily.

Figure 10A:
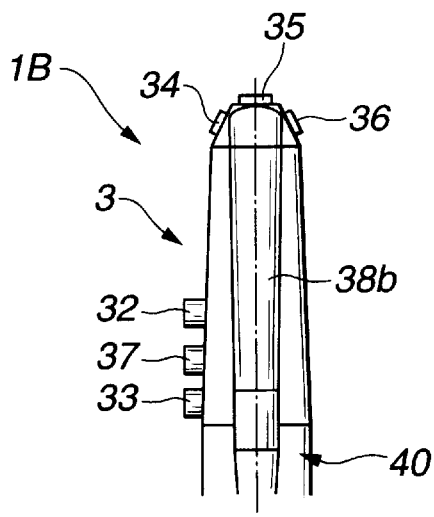
FIG. 10A and FIG. 10B are explanatory diagrams concerning the structure of a joint between the operation unit of the electronic endoscope and a universal cord thereof.
Figure 10B:
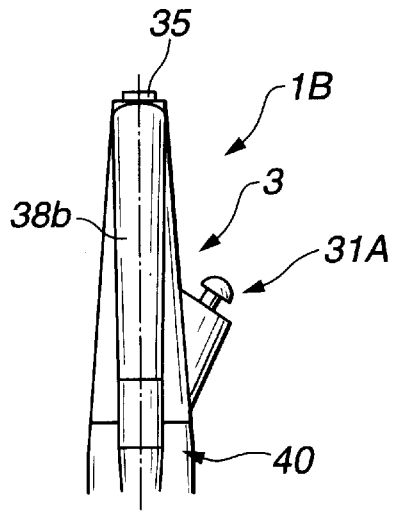

As shown in FIG. 10A and FIG. 10B, in an endoscope 1B, a cord juncture 38b projected from the operation unit 3 and the operation unit 3 share the same plane. The insertion unit 2 extending from the operation unit 3 and the universal cord 4 can be balanced more easily.

Figure 11A:
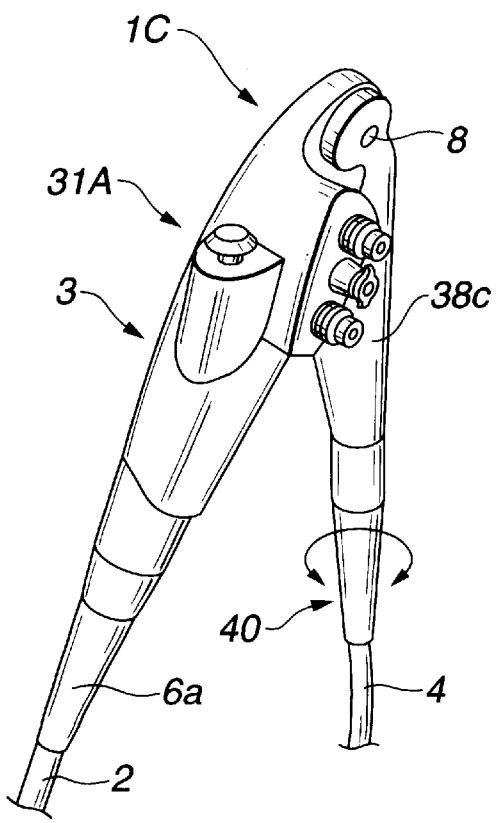
FIG. 11A and FIG. 11B are explanatory diagrams concerning the structure of another joint between the operation unit of the electronic endoscope and the universal cord thereof.
Figure 11B:
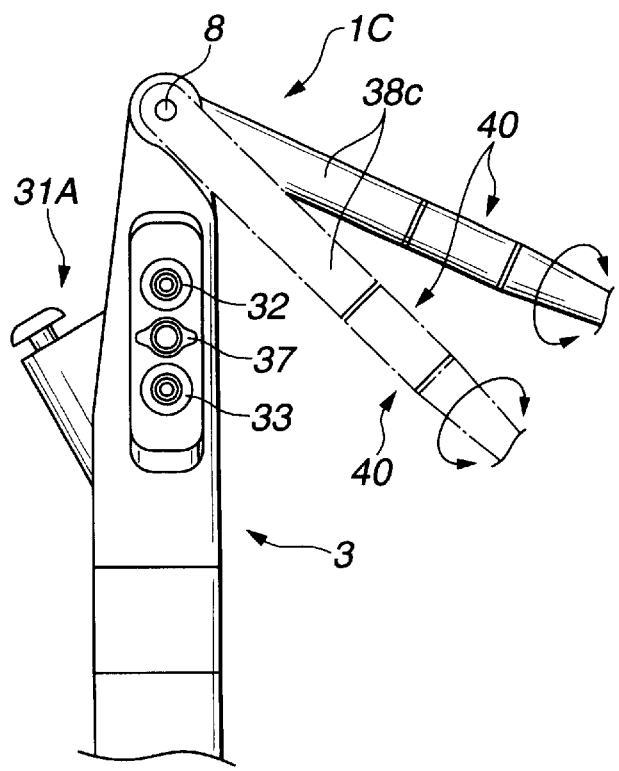

Moreover, as shown in FIG. 11A and FIG. 11B, in an endoscope 1C, the operation unit 3 and a cord juncture 38c are joined using a hinge 8 serving as an angle varying means so that the cord juncture 38c can pivot freely. This results in a hold assistant composed of the cord juncture 38c and coupling fixture 40 that are located at any desired position by varying an angle θ depending on the size of an operator's hand or operator's likes or dislikes. Thus, the endoscope 1C offers further improved maneuverability.

According to the present invention, it is apparent that a wide range of different embodiments can be constructed based on the invention without a departure from the spirit and scope of the invention. The present invention will be limited by the appended claims but not restricted to any specific embodiment.

What is claimed is:

1. An easily maneuverable electronic endoscope comprising:
    an operation unit having a treatment appliance insertion port, a longitudinal direction, and various operation switches and filling the role of a hand-held unit;
    an elongated insertion unit extending from a lower end of said operation unit in a direction substantially corresponding to the longitudinal direction of said operation unit; and
    a universal cord extending from an upper part of said operation unit in a direction crossing the longitudinal direction of said operation unit at an acute angle, and accommodating at least a signal cable, and said universal cord being rotatably coupled to said operation unit.

2. An electronic endoscope according to claim 1, wherein a portion proximal to said universal cord is joined to the proximal end of said operation unit at an acute angle with respect to the longitudinal axis of said operation unit so that the longitudinal axis of said universal cord will cross the longitudinal axis of said operation unit at an acute angle.

3. An electronic endoscope according to claim 2, wherein the longitudinal axis of said universal cord and the longitudinal axis of said operation unit share the same plane.

4. An electronic endoscope according to claim 2, further comprising an angle varying means linking said operation unit and universal cord and making it possible to vary a crossed-axes angle formed between a portion proximal to said universal cord and said operation unit, wherein:
    the crossed-axes angle is varied in order to allow the portion proximal to said universal cord to abut against the back of a user's hand with which said operation unit is held irrespective of the size of the user's hand.

5. An electronic endoscope according to claim 1, further comprising an angle varying means linking said operation unit and universal cord and making it possible to vary a crossed-axes angle formed between a portion proximal to said universal cord and said operation unit, wherein:
    the crossed-axes angle is varied in order to allow the portion proximal to said universal cord to abut against the back of a user's hand with which said operation unit is held irrespective of the size of the user's hand.

6. An electronic endoscope according to claim 5, wherein said angle varying means is a hinge for joining said cord juncture to said operation unit so that said cord juncture can pivot freely.

7. An easily maneuverable electronic endoscope comprising:
    an operation, unit having a treatment appliance insertion port, a longitudinal direction, and various operation switches and filling the role of a hand-held unit;

an elongated insertion unit extending from a lower end of said operation unit in a direction substantially corresponding to the longitudinal direction of said operation unit; and a universal cord extending from an upper part of said operation unit in a direction crossing the longitudinal direction of said operation unit at an acute angle, and accommodating at least a signal cable;

wherein a portion proximal to said universal cord meeting said operation unit at an acute angle serves as a hold assistant against which the back of a user's hand with which said operation unit is held is rested.

8. An easily maneuverable electronic endoscope comprising:

an operation unit having a treatment appliance insertion port, a longitudinal direction, and various operation switches and filling the role of a hand-held unit;

an elongated insertion unit extending from a lower end of said operation unit in a direction substantially corresponding to the longitudinal direction of said operation unit;

a universal cord extending from an upper part of said operation unit in a direction crossing the longitudinal direction of said operation unit at an acute angle, and accommodating at least a signal cable; and a cord twist correcting structure, formed on said operation unit, for linking said operation unit and universal cord and permitting said universal cord to freely rotate at least 180° about the axis of said universal cord, wherein:

even when said universal cord have such a positional relationship to said operation unit that it is twisted to form a twist, once said universal cord is rotated, the twist is unraveled.

9. An electronic endoscope according to claim 8, wherein said cord twist correcting means comprises:

a cord juncture projecting from said operation unit and having a screw hole on the wall of which a female screw to be mated with a lock screw is threaded; and a coupling fixture including a first coupling member that has a rotator portion joined to said cord juncture so that it can rotate freely, and a second coupling member that is joined to said first coupling member as an integral part of said first coupling member and in which said universal cord is locked as an integral part of said second coupling member.

10. An easily maneuverable electronic endoscope comprising:

an operation unit having a treatment appliance insertion port, a longitudinal direction, and various operation switches and filling the role of a hand-held unit;

an elongated insertion unit extending from a lower end of said operation unit in a direction substantially corresponding to the longitudinal direction of said operation unit; and a universal cord extending from an upper part of said operation unit in a direction crossing the longitudinal direction of said operation unit at an acute angle, and accommodating at least a signal cable;

wherein a treatment appliance insertion port is interposed between an aeration/perfusion button and a suction button that comprise operation switches formed on said operation unit.

11. An electronic endoscope comprising:

an operation unit having a longitudinal direction associated therewith, and an elongated insertion unit extending from a lower end of the operation unit in a direction corresponding to the longitudinal direction of said operation unit; and a universal cord extending in a direction crossing the longitudinal direction of said operation unit at an acute angle, wherein a portion of said universal cord extending from said operation unit serves as a hold assistant against which the back of an operator's hand with which said operation unit is held is rested.

12. An endoscope, comprising:

a hand-held operation unit having at least one operation switch associated therewith, said operation unit having a longitudinal axis;

an elongated insertion unit extending from said operation unit; and a signal cord extending from said operation unit through an elongated rigid member which is fixed to said operation unit, at least a portion of said rigid member being located opposite a side surface of said operation unit and extending along a substantially straight line which forms an acute angle with said longitudinal axis of said operation unit, and said signal cord being rotatably coupled to said operation unit.

13. An endoscope according to claim 12, wherein said portion of said rigid member and said side surface of said operation unit form space in which a hum,an operator's hand may be inserted.

14. An endoscope according to claim 13, wherein said space is of a size adapted to accommodate a human operator's hand such that the palm of said human operator's hand can grasp said side surface of said operation unit and the back of said human operator's hand can touch said rigid member.

15. An endoscope according to claim 12, wherein said rigid member comprises:

a cord junction which is fixedly coupled to said operation unit; and a coupling fixture which is rotatably coupled to said cord junction.

16. An endoscope according to claim 15, wherein said signal cord is fixedly coupled to said coupling fixture and is thereby rotatably coupled to said cord junction and said operation unit.

17. An endoscope according to claim 16, wherein said coupling fixture comprises first and second coupling members which are removably connected to one another, and which form a recess which receives said cord junction.

18. An endoscope according to claim 17, wherein a rotation groove extends circumferentially in said first coupling member, said first coupling member is engaged with said cord junction by a lock screw meshed with a screw hole in said cord junction and said lock screw is received by said rotation groove.

19. An endoscope according to claim 18, wherein said rotation groove enables said cord to rotate less than 360°.

20. An endoscope according to claim 19, wherein an O ring is located between said cord junction and said coupling fixture to prevent water permutation.

21. An endoscope according to claim 12, wherein said signal cord has a signal line adapted to carry information signals therein.

22. An endoscope according to claim 12, wherein said signal cord has a fiber optic line extending therethrough.

23. An endoscope according to claim 12, wherein said signal cord is operatively coupled to said elongated insertion unit.

24. An endoscope according to claim 23, wherein signals pass between said elongated insertion unit and said signal cord.

25. An endoscope according to claim 12, wherein said operation unit also includes a treatment appliance insertion port.

26. An endoscope according to claim 12, wherein said elongated insertion unit exits said operation unit along said longitudinal axis.

27. An endoscope according to claim 26, wherein said elongated insertion unit is a flexible unit.

28. An endoscope according to claim 27, wherein said elongated insertion unit extends from said operation unit through a second rigid member which extends from said operation unit along said longitudinal axis.

29. An endoscope, comprising:
a hand-held operation unit having at least one operation switch associated therewith, said operation unit having a longitudinal axis;
an elongated insertion unit extending from said operation unit; and
a signal cord extending from said operation unit through an elongated rigid member which is fixed to said operation unit, at least a portion of said rigid member being located opposite a side surface of said operation unit and extending along a substantially straight line which forms an acute angle with said longitudinal axis of said operation unit;
wherein said portion of said rigid member forms an acute angle with said longitudinal axis in at least two planes.

30. An endoscope, comprising:
an elongated hand-held operation unit having at least one operation switch associated therewith;
an elongated insertion unit extending from said operation unit; and
a signal cord extending from said operation unit through an elongated rigid member which is fixed to said operation unit, at least a portion of said rigid member having a surface opposed to a side surface of said operation unit and forming a space in which a human operator's hand can be placed where the palm of the human operator's hand can grasp said side surface of said operation unit and the back of said human operator's hand can touch said rigid member, said signal cord being rotatably coupled to said operation unit.

31. An endoscope according to claim 30 further comprising a hinge coupled to said cord junction and said operation unit.

32. An endoscope according to claim 31, wherein said hinge permits said space to be adjusted.

33. An endoscope according to claim 30, wherein said rigid member comprises:
a cord junction which is fixedly coupled to said operation unit; and
a coupling fixture which is rotatably coupled to said cord junction.

34. An endoscope according to claim 33, wherein said signal cord is fixedly coupled to said coupling fixture and is thereby rotatably coupled to said cord junction and said operation unit.

35. An endoscope according to claim 34, wherein said coupling fixture comprises first and second coupling members which are removably connected to one another, and which form a recess which receives said cord junction.

36. An endoscope according to claim 35, wherein a rotation groove extends circumferentially in said first coupling member, said first coupling member is engaged with said cord junction by a lock screw meshed with a screw hole in said cord junction and said lock screw is received by said rotation groove.

37. An endoscope according to claim 36, wherein said rotation groove enables said cord to rotate less than 360°.

38. An endoscope according to claim 37, wherein an O ring is located between said cord junction and said coupling fixture to prevent water permutation.

39. An endoscope according to claim 30, wherein said signal cord has a signal line adapted to carry information signals therein.

40. An endoscope according to claim 30, wherein said signal cord has a fiber optic line extending therethrough.

41. An endoscope according to claim 30, wherein said signal cord is operatively coupled to said elongated insertion unit.

42. An endoscope according to claim 41, wherein signals pass between said elongated insertion unit and said signal cord.

43. An endoscope according to claim 30, wherein said operation unit also includes a treatment appliance insertion port.

44. An endoscope according to claim 30, wherein said elongated insertion unit exits said operation unit along said longitudinal axis.

45. An endoscope according to claim 44, wherein said elongated insertion unit is a flexible unit.

46. An endoscope, comprising:
an elongated hand-held operation unit having at least one operation switch associated therewith;
an elongated insertion unit extending from said operation unit; and
a signal cord extending from said operation unit through an elongated rigid member which is fixed to said operation unit, at least a portion of said rigid member having a surface opposed to a side surface of said operation unit and forming a space in which a human operator's hand can be placed where the palm of the human operator's hand can grasp said side surface of said operation unit and the back of said human operator's hand can touch said rigid member;
wherein said portion of said rigid member forms an acute angle with said operation unit in at least two planes.

* * * * *